(12) United States Patent
Musal et al.

(10) Patent No.: US 7,797,765 B2
(45) Date of Patent: Sep. 21, 2010

(54) LENS REPLACEMENT SYSTEM

(75) Inventors: Michael J. Musal, Soquel, CA (US);
Craig M. Lawrence, Menlo Park, CA (US); Aaron A. Henningsgaard, Palo Alto, CA (US); Eamon Briggs, Santa Cruz, CA (US)

(73) Assignee: Bell Sports, Inc., Scotts Valley, CA (US)

( * ) Notice: Subject to any disclaimer, the term of this patent is extended or adjusted under 35 U.S.C. 154(b) by 826 days.

(21) Appl. No.: 11/617,291

(22) Filed: Dec. 28, 2006

(65) Prior Publication Data

US 2007/0153230 A1 Jul. 5, 2007

Related U.S. Application Data

(60) Provisional application No. 60/755,622, filed on Dec. 30, 2005.

(51) Int. Cl.
*A61F 9/02* (2006.01)
(52) U.S. Cl. .......................................................... 2/448
(58) Field of Classification Search ............. 2/448–451, 2/438; 351/86
See application file for complete search history.

(56) References Cited

U.S. PATENT DOCUMENTS 3,383,707 A * 5/1968 McNeill .......................... 2/12
3,896,496 A 7/1975 Leblanc et al. ................... 2/14
4,689,838 A * 9/1987 Angermann et al. ........... 2/441
5,379,464 A * 1/1995 Schleger et al. ................ 2/431
5,815,235 A 9/1998 Runckel
6,086,199 A * 7/2000 Holland et al. ................ 351/86
6,224,209 B1 * 5/2001 Chen ............................ 351/86
6,665,885 B2 12/2003 Masumoto ..................... 2/436
6,732,383 B2 5/2004 Cleary et al. ................... 2/450
6,742,890 B1 * 6/2004 Teng ............................ 351/86
2004/0025232 A1 2/2004 Hartley et al.
2005/0036104 A1 * 2/2005 Howard et al. ............... 351/131
2006/0191062 A1 * 8/2006 Matera .......................... 2/426
2007/0261155 A1 * 11/2007 Tabacchi ....................... 2/439

OTHER PUBLICATIONS

European Patent Office, Germany, European Search Report for Application No. 06256623.7-2310, Reference JL37348P, Mailed May 7, 2007, 7 pages.
Scrim; "Carrera 06-07," http://www.biglines.com/articles_readmore.php?article=10&read=2881; 2 pages, Apr. 26, 2006.
"Carrera, (Products)," http://www.carrerasportusa.com/highlights.php?languageid=2; one page.
European Office Action, Application No. 06 256 623.7, 2 pages.

* cited by examiner

*Primary Examiner*—Katherine Moran
(74) *Attorney, Agent, or Firm*—Baker Botts L.L.P.

(57) ABSTRACT

An eyewear system includes a frame having a lens channel configured to slidably receive the lens and an opening to allow the lens to be inserted into the lens channel. The system further includes a lens configured to be slidably received into the lens channel of the frame and a latch to releasably secure the lens in the frame.

6 Claims, 8 Drawing Sheets

LENS REPLACEMENT SYSTEM

CROSS-REFERENCE TO RELATED APPLICATIONS

This application claims benefit under 35 U.S.C. §119(e) of U.S. Provisional Application Ser. No. 60/755,622 filed Dec. 30, 2005 entitled Lens Replacement System and Method.

TECHNICAL FIELD OF THE INVENTION

This invention relates in general to eyewear and more particularly to a lens replacement system.

BACKGROUND OF THE INVENTION

Users of eyewear, such as goggles used for snow sports and other activities, may desire to replace the lens or lenses in the eyewear for various reasons. For example, a user may wish to change the tint of the lens being used based on particular sunlight conditions. A user may also desire to replace a damaged lens. As another example, a user may want to change the lens for fashion purposes.

While several goggles produced today permit lens replacement, the process is time-consuming and not user-friendly. Specifically, such goggles often use a "snap fit" lens that is popped into and out of the frame of the goggles by plastic deformation. Replacing the lens in such goggles is difficult as it requires a large amount of force to remove the lens and significant dexterity to insert a new lens. Moreover, goggles using the snap-fit replacement require the user to touch the lens surface which can create scratches or fingerprint marks on the lens.

SUMMARY OF EMBODIMENTS OF THE INVENTION

From the foregoing, it may be advantageous to provide eyewear, such as goggles, that offer a quick, user-friendly lens replacement system that does not require any touching of the lens. In accordance with the present invention, a quick change lens replacement system is provided that substantially eliminates or greatly reduces disadvantages associated with prior lens replacement techniques.

In accordance with a particular embodiment of the present invention an eyewear system includes a frame, lens, and latch. The frame has a lens track configured to slidably receive a lens and the lens is configured to be slidably received into the lens track. The latch is functional to secure the lens in the frame.

In a particular embodiment, the eyewear system further includes a top rail affixed to the lens. The top rail provides a gripping means so that the lens can be inserted and removed without touching the surface. In certain embodiments, the top rail is associated with the latch in securing the lens in the frame.

In accordance with another embodiment of the present invention, the eyewear system includes outriggers pivotally associated with the frame. One function of the outriggers is to secure the lens in the frame. The outriggers are further functional to enable the goggles to accommodate a variety of head and helmet sizes by rotating according to the pull of the head strap.

Technical advantages of particular embodiments of the present invention include an ability to easily replace a lens in goggles. Quick lens replacement allows a user to adapt the goggles to changing conditions. For instance, the intensity of the sunlight may vary, or the lens may get damaged while in use. Another advantage of particular embodiments of the present invention is that it enables lens replacement without touching the lens surface. Thus, a user can change a lens without leaving fingerprints or scratches.

Other technical advantages will be readily apparent to one skilled in the art from the following figures, descriptions, and claims. Moreover, while specific advantages have been enumerated above, various embodiments may include all, some or none of the enumerated advantages.

BRIEF DESCRIPTION OF THE DRAWINGS

To provide a more complete understanding of the present invention and the features and advantages thereof, reference is made to the following description, taken in conjunction with the accompanying drawings in which.

DETAILED DESCRIPTION OF THE INVENTION

Figure 1A:
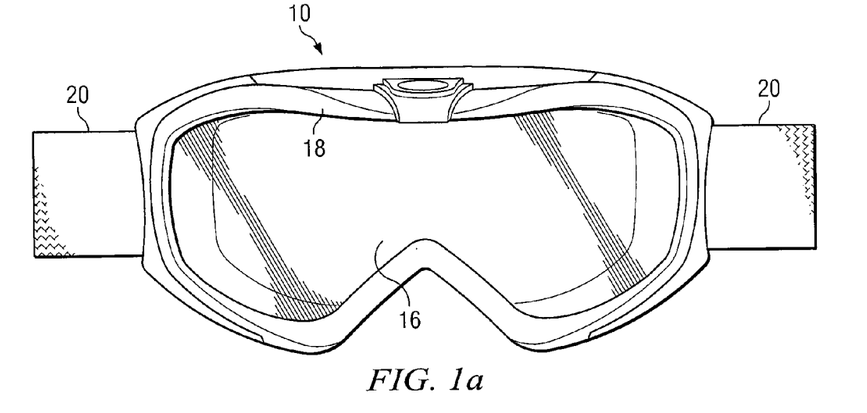
FIGS. 1(a) and 1(b) are drawings illustrating unexploded and exploded views, respectively, of goggles incorporating a quick change lens replacement system.
Figure 1B:
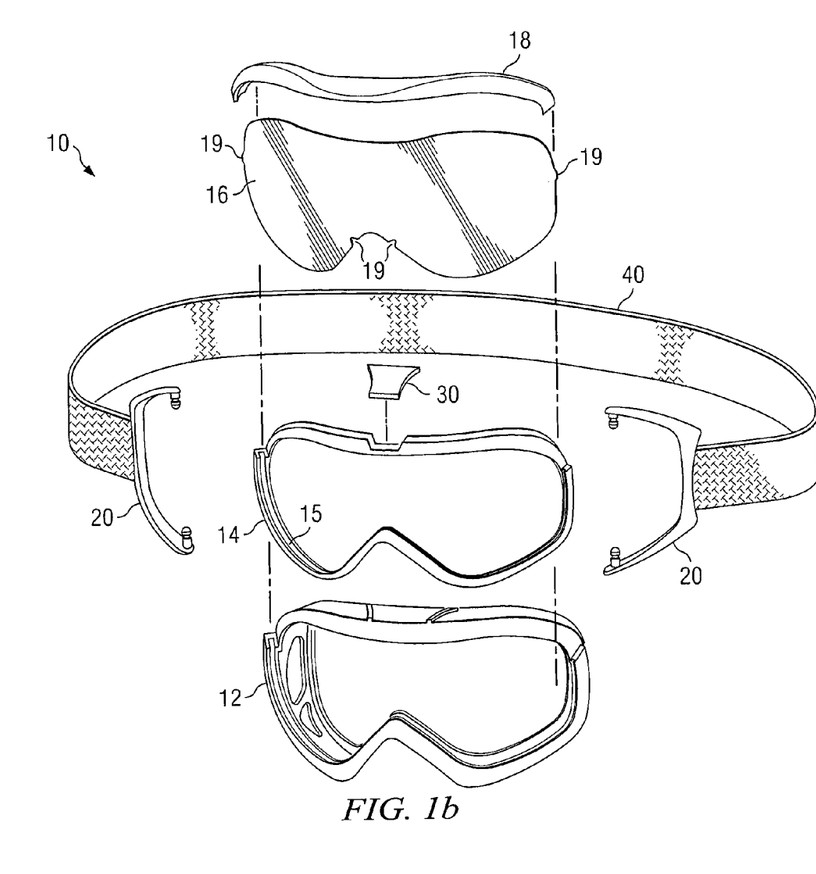

FIGS. 1(a) and 1(b) illustrate exploded and unexploded views of goggles 10 featuring a quick change lens replacement system in accordance with one embodiment of the present invention. Goggles 10 are functional to protect the facial region and eyes when a user is engaged in activities such as snow skiing, snowboarding, wakeboarding, water skiing, snowmobiling, or motor sports such as motocross. In the illustrated embodiment, goggles 10 comprise frame 12, lens support 14, and lens 16.

In accordance with a particular embodiment of the invention, lens 16 is readily removable and replaceable. More particularly, lens 16 is slidably associated with lens support 14 which provides a lens channel 15 for inserting and removing lens 16. Lens/top rail assembly 17 comprises top rail 18 affixed to the upper edge of lens 16. Top rail 18 provides a gripping means for a user to grasp when inserting and removing lens 16. Thus, top rail 18 further serves to enable lens replacement without requiring any touching of lens 16. Accordingly, several technical advantages of the present invention are readily apparent.

Lens 16 may serve many functions such as protecting the facial region, blocking sunlight, and preventing exposure to ultra-violet ("UV") rays. Given the myriad of potential uses for goggles 10, lens 16 could embody numerous shapes. For instance, lens 16 might be flat, curved, square, round, ovular, or any combination thereof. Lens 16 may be manufactured from a variety of materials including, but not limited to, polycarbonate, acrylic, or CR-39. Further, lens 16 may be photochromatic, polarized, or tinted, to provide a range of light attenuation and color filtration.

Lens 16 may also include a number of snap features 19 which engage with snap details in lens channel 15. As illustrated, snap features 19 shown as: two snaps at the nose and one each on either edge of the lens. In an embodiment of the present invention, the snap details in lens channel 15 are matingly associated with snap features 19, thereby aligning and securing lens 16 in lens channel 15. It should be noted that while Snap features 19 help align and secure lens 16 in lens channel 15, they are light enough to easily be overcome by pressing the top rail 18 (when inserting the lens) or pulling on top rail (when removing the lens).

Although lens 16 is referred to as singular, it may constitute a plurality of lenses. For example, lens 16 may be a sealed double lens with an airspace in between. A double lens structure may be desirable to prevent fogging or provide extra UV protection. Moreover, while lens 16 is illustrated as a unitary structure, it may also constitute a plurality of pieces.

In the illustrated embodiment, frame 12 is a dual-material structure comprised of lens support 14 over-molded with a supple casing that forms the outer surface of frame 12. Lens support 14 functions as an internal skeleton providing sufficient rigidity to provide a lens channel 15 for sliding lens 16 into and out of frame 12. Accordingly, lens support 14 may be one of several suitable materials such as a high durometer thermoplastic polyurethane (TPU). As illustrated, the over-molded casing is a low durometer TPU, however one skilled in the art would readily recognize that the over-molded casing could be any number of suitable materials such as polypropylene, polyethylene, any rubber, or elastomeric material.

Goggles 10 further include outriggers 20 and fastener 30. Outriggers 20 and fastener 30 are operable to releasably secure lens 16 in frame 12. More particularly, outriggers 20 and fastener 30 lock lens 16 in place such that it cannot be removed without some user operation. Thus, a user of goggles 10 may engage in a variety of high impact activities without lens/top rail assembly 17 becoming dislodged from frame 12. Although FIGS. 1(*a*) and 1(*b*) depict goggles 10 as including both fastener 30 and outriggers 20, one skilled in the art would readily recognize that the lens replacement system of the present invention is functional with only one of such features. Thus, particular embodiments may only include one or the other of these securing feature.

Goggles 10 also include a head strap 40 which is typically an elastic material. The ends of head strap 40 may be attached to outriggers 20. Alternatively, the ends of head strap 40 may be attached to frame 12. In operation, head strap 40 encircles the head of the user and is functional to secure goggles 10 to the face of a user. Head strap 40 may include an adjustment mechanism to modify its length and/or adjust tension.

FIGS. 2-9 illustrate various versions of a quick change lens replacement system in accordance with particular embodiments of the present invention. FIGS. 2-5 illustrate particular embodiments using outriggers as a securing mechanism for lens/top rail assembly 17, whereas FIGS. 6-9 illustrate various embodiments of the system implemented using a top-mounted fastener as securing mechanisms. It should be noted that these features may be combined in suitable embodiments.

Figure 2A:
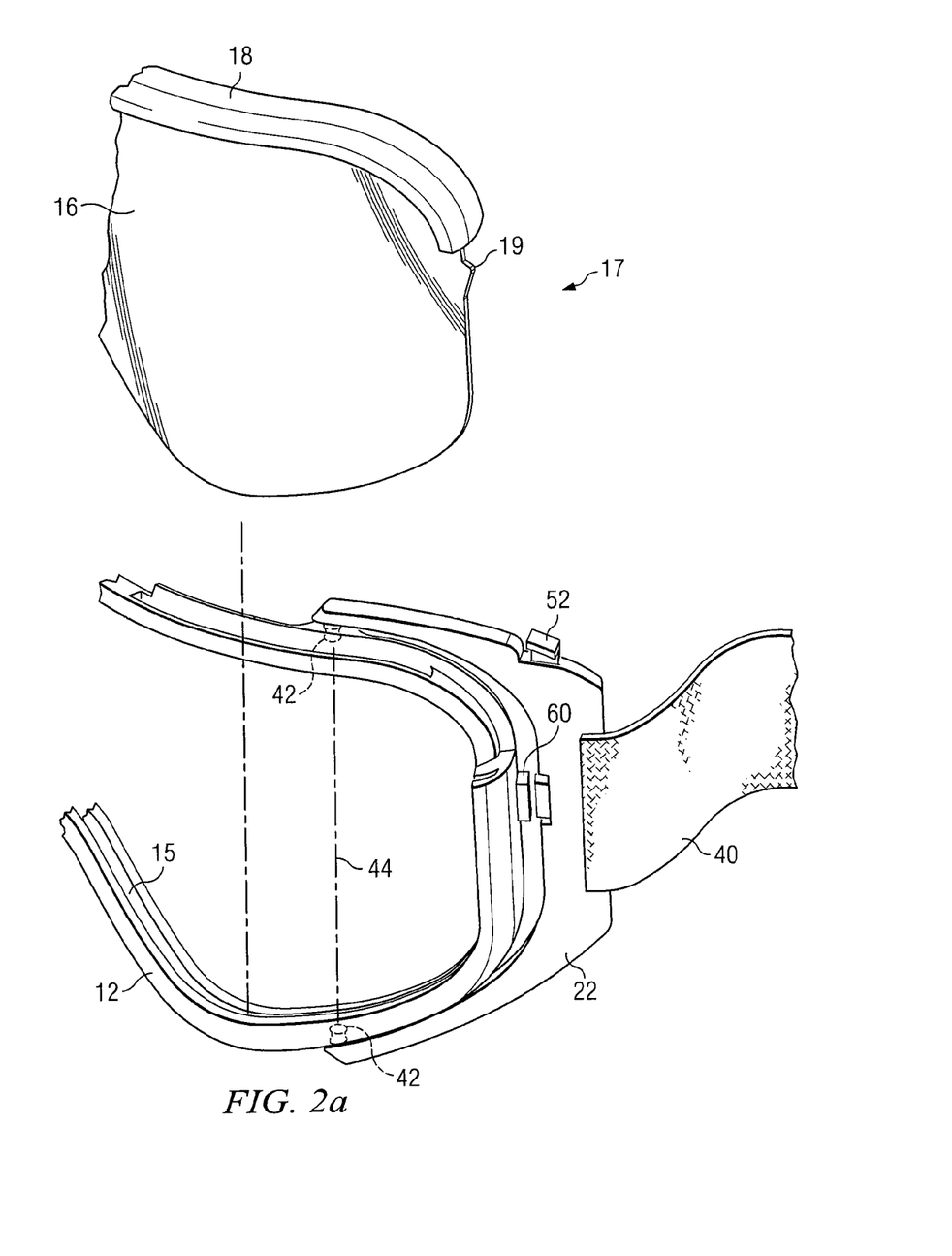
FIG. 2 is a drawing illustrating an embodiment of a lens replacement system implemented using an outrigger.
Figure 2B:
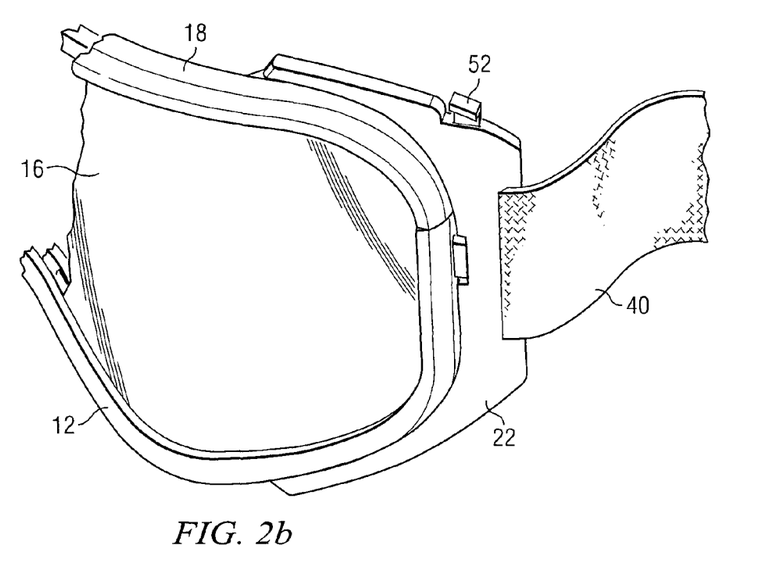

With reference to FIG. 2, depicted is one embodiment of the lens replacement system implemented using outrigger 22. While a single outrigger 22 is depicted, the goggles may include a corresponding outrigger 22 affixed to the opposite side of the goggles (not shown). Outrigger 22 is rotatable about axis 44 extending through outrigger mounting points 42. When outrigger 22 is rotated into a forward position it overlies a portion of top rail 18 thereby securing lens/top rail assembly 17 in place. As used herein, "forward" references the direction away from the user's face when the goggles are affixed to the user's head. Correspondingly, "rearward" references the direction toward the user's face when the goggles are properly affixed to the user's head.

Outrigger 22 is locked in a forward position by latch 52 and flange 60. As illustrated, latch 52 is included within outrigger 22 and is spring loaded in a locked position. Flange 60 is fashioned such that when outrigger 22 is rotated forward, flange 60 forces latch 52 to move inward in outrigger 22, thereby allowing outrigger 22 to pass the plane of flange 60. Once outrigger 22 rotates past the plane of flange 60, latch 52 returns to a locked position. At this point, outrigger 22 is in the "locked forward" position. From a locked forward position, a user must manually release latch 52 to enable outrigger 22 to rotate rearwardly past the plane of flange 60. Accordingly, once outrigger 22 rotates forward past the plane of flange 60, lens/top rail assembly 17 is securely locked in place.

As described, when outrigger 22 is in a locked forward position, it is restrained from rotating rearwardly past the plane of flange 60. However, outrigger 22 may continue to rotate forward through a set angle. In the illustrated embodiment, outrigger 22 is able to rotate up to fifteen degrees past the plane of flange 60 in the forward direction. Permitting continued forward rotation allows head strap 40 affixed to outrigger 22 to securely fit the goggles to a variety of helmet or head sizes. When a user with a small helmet, or no helmet at all, puts on the goggles the tension in head strap 40 might force outrigger 22 into the locked position where latch 52 is flush against flange 60. By contrast, if the user is wearing a bulky helmet, or has a large head, the tension in head strap 40 might pull outrigger 22 forward to compensate for the shape. Such adjustment allows the goggles to accommodate a variety of user head and helmet sizes.

In the present embodiment, removal of lens/top rail assembly 17 when outrigger 22 is positioned in a locked forward position requires the user to manually release latch 52 while simultaneously rotating outrigger 22 rearwardly past the plane of flange 60. In the illustrated embodiment, manually releasing latch 52 entails exerting a force on the upper portion of latch 52 which is counter to the spring loaded direction. Once outrigger 22 is rotated past the plane of flange 60, a user may remove lens/top rail assembly 17 by pulling on top rail 18 and sliding lens 16 out from frame 12. A new lens 16 can be inserted by sliding lens/top rail assembly 17 into frame 12 by pushing on top rail 18. Accordingly, no touching of the lens surface is required to insert or remove a lens. Furthermore, the user need only release latch 52 to unsecure the lens for removal. Thus, several advantages of the present invention are apparent.

While FIG. 2 illustrates the lens replacement system of the present invention using latch 52 and flange 60 to lock outrigger 22 in a forward position, one skilled in the art will recognize that numerous potential mechanisms could be used. By means of example and not limitation, suitable mechanisms are illustrated in the subsequent embodiments.

Figure 3:
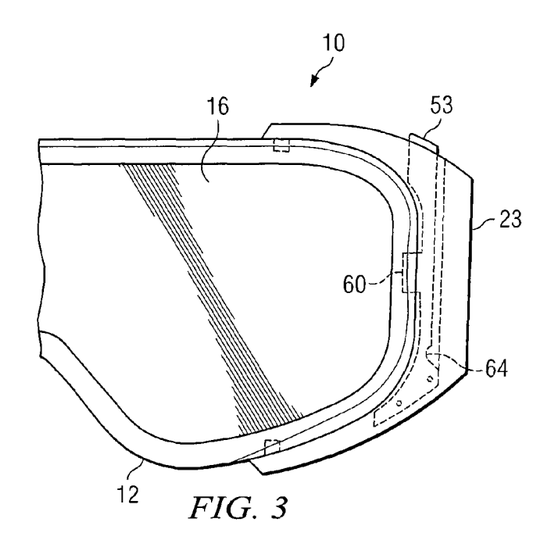
FIG. 3 is a drawing illustrating a variation of an outrigger forward locking mechanism.

FIG. 3 illustrates one such outrigger forward locking mechanism implemented with the lens replacement system of the present invention. As represented in FIG. 3, outrigger 23 operates in substantially the same manner as outrigger 22 in FIG. 2, however it uses a different latching mechanism. Specifically, in this embodiment, latch 53 incorporates a built in flex point 64 (instead of using a spring as in latch 52 of FIG. 2). Latch 53 is released by moving the top portion of latch 53 outward which causes latch 53 to bend at flex point 64. Bending latch 53 about flex point 64 provides sufficient clearance to permit the body of latch 53 to pass by flange 60.

Figure 4A:
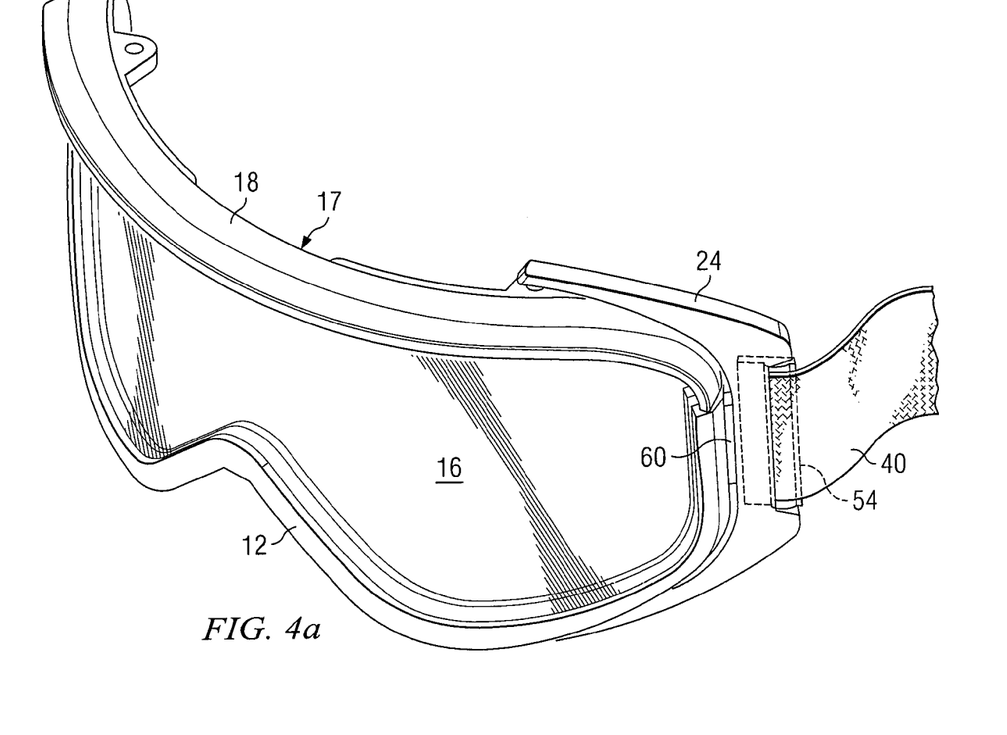
FIGS. 4(a) and 4(b) are drawings illustrating another variation of an outrigger forward locking mechanism.
Figure 4B:
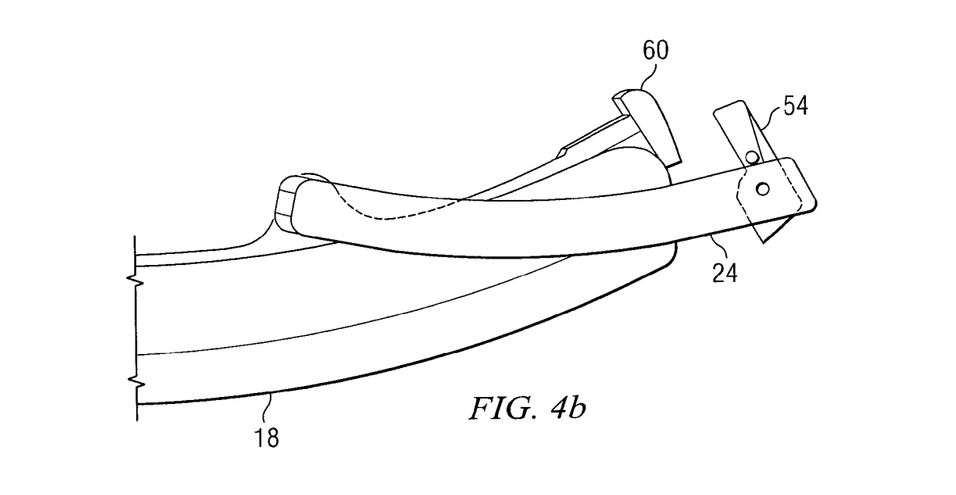

FIG. 4 illustrates another embodiment of a mechanism for placing an outrigger in a locked forward position in accordance with the quick change lens replacement system of the present invention. This embodiment operates in a manner substantially similar to the previously disclosed outrigger based lens replacement systems, but incorporates a different latching mechanism. As illustrated, latch 54 is mounted to outrigger 24 and connected to head strap 40. Latch 54 is functional to rotate between an open and closed position. To remove lens/top rail assembly 17 when outrigger 24 is in a locked forward position, a user pulls forward on head strap 40. Pulling head strap 40 forward causes latch 54 to rotate forward and release from flange 60. Thus, outrigger 24 is permitted to rotate into a rearward position, thereby freeing top rail 18. At this point, lens/top rail assembly 17 may be slidably removed from frame 12. As with the previous embodiments, when outriggers 24 are in the rearward position, lens/top rail 17 can also be inserted into frame 12.

In the embodiment of the present invention illustrated in FIG. 4, securing lens/top rail assembly 17 to frame 12 only requires rotating outriggers 24 forward. The forward rotation of outriggers 24 brings flange 60 into contact with latch 54 thereby causing latch 54 to rotate forward. Once the distal edge of latch 54 passes the plane of flange 60, outriggers 54 are in a locked forward position. At this point, if outriggers 24 are rotated rearwardly latch 54 will catch on flange 60 thereby preventing further rearward rotation of outriggers 24. As with the previous outrigger based lens replacement systems, outriggers 24 are still permitted to rotate in a forward direction to a set angle.

Figure 5A:
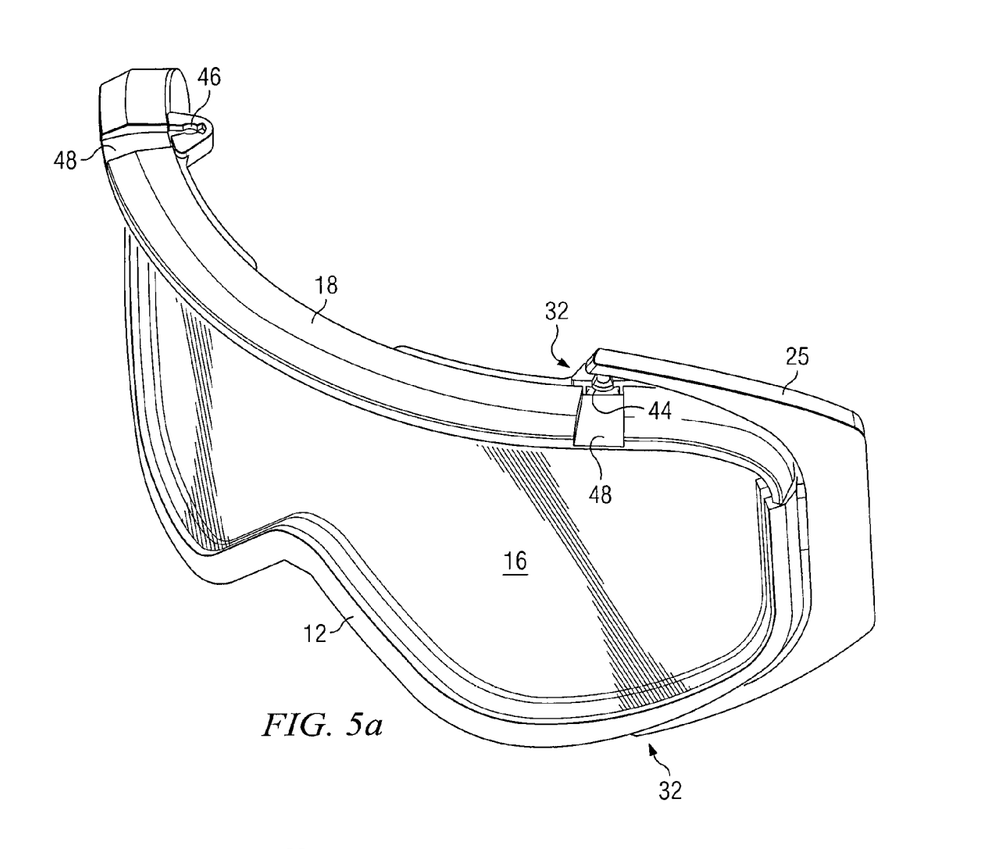
FIGS. 5(a) and 5(b) are drawings illustrating yet another outrigger embodiment of the lens replacement system.
Figure 5B:
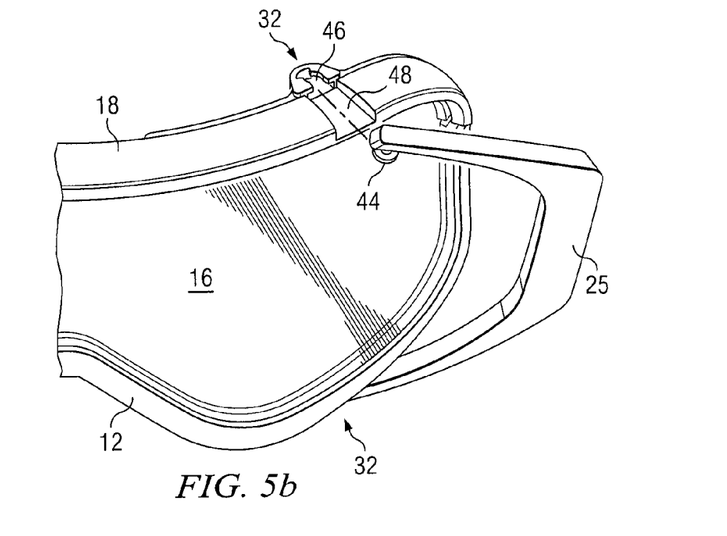

FIGS. 5(a) and 5(b) illustrate another embodiment of the system of the present invention implemented using an outrigger. In this embodiment, outrigger 25 is able to detach from frame 12 at the upper mounting point. Detaching outrigger 25 from frame 12 opens a path for lens/top rail assembly 17 to be inserted or removed. When outrigger 25 is detached from frame 12 at the upper mounting point, it remains attached to the frame at the lower mounting point. In a particular embodiment of the present invention, the lower mounting point is constructed as a ball joint to allow the outrigger to pivot out of the insertion/removal path of 17 lens/top rail assembly.

Referring to FIG. 5(a), outrigger 25 is connected to frame 12 at upper and lower mounting points 32. As illustrated, outrigger mounting point 44 has a peg contour associated with keyhole 46. Outrigger mounting point 44 is able to move in and out of keyhole 46 along guide path 48. Guide path 48 is located on top rail 18 and functions to guide mounting point 44 when it is inserted or removed from keyhole 46.

In operation, keyhole 46 functions to maintain outrigger 25 in a locked forward position. When the goggles are properly positioned on the users face, head strap 40 will naturally pull outrigger 25 rearwardly. The positioning of keyhole 46 may be such that the pull of head strap 40 on outrigger 25 will be at an angle of at least ninety degrees to the direction of entry of outrigger mounting point 44. Accordingly, outrigger mounting point 44 is prevented from exiting keyhole 46 when the goggles are on the user's face.

The range of motion of outrigger 25 is substantially similar to the aforementioned outrigger embodiments of the present invention. More particularly, outrigger 25 is restrained from rotating rearwardly by flange 60. Thus, when outrigger mounting point 44 is situated in keyhole 46 lens/top rail assembly 17 is secured to frame 12. Further, outrigger 25 is also permitted to rotate a set angle past flange 60 in the forward direction to accommodate helmets of various sizes.

Figure 6:
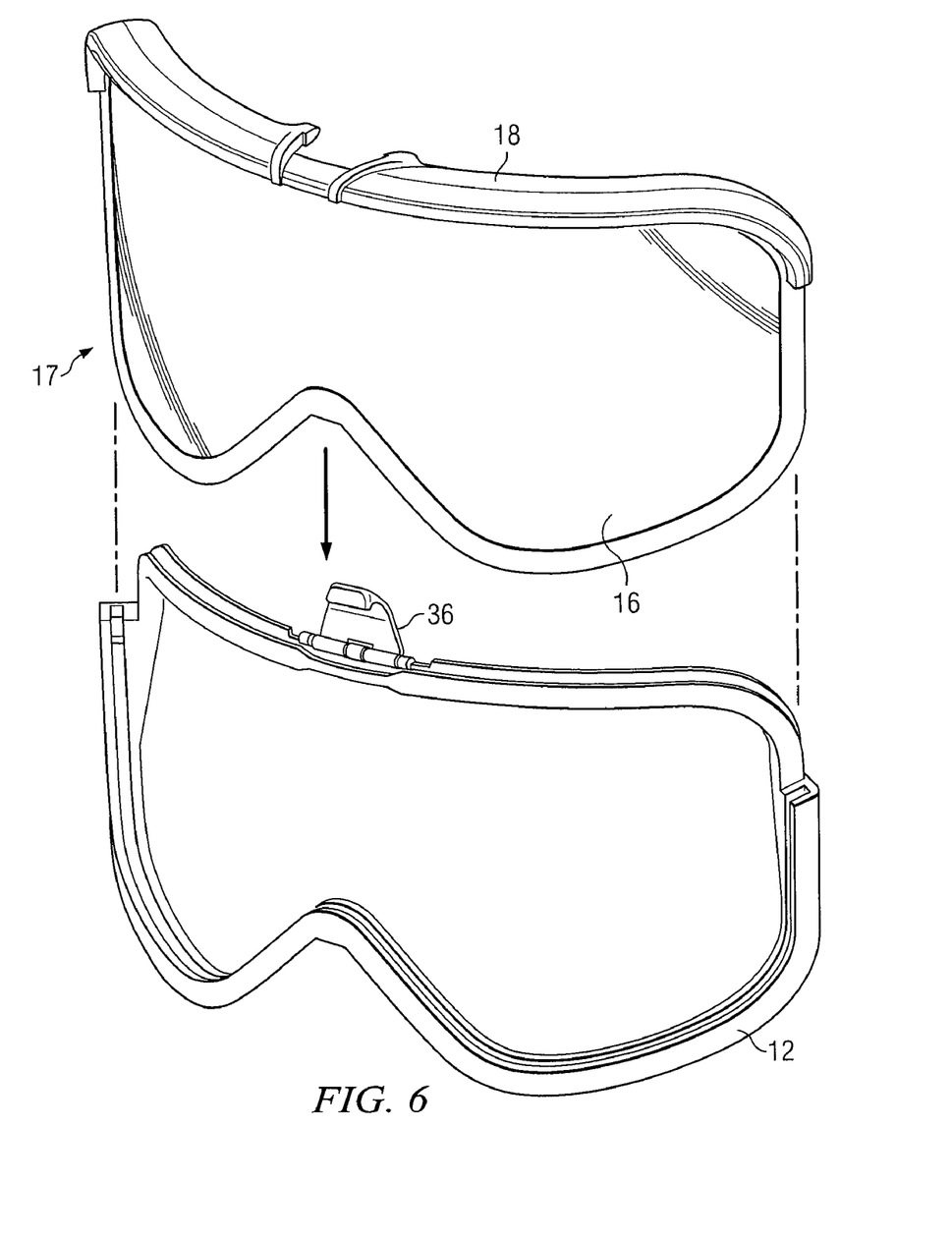
FIG. 6 is a drawing illustrating an embodiment of a lens replacement system incorporating a top-mounted fastener.
Figure 7A:
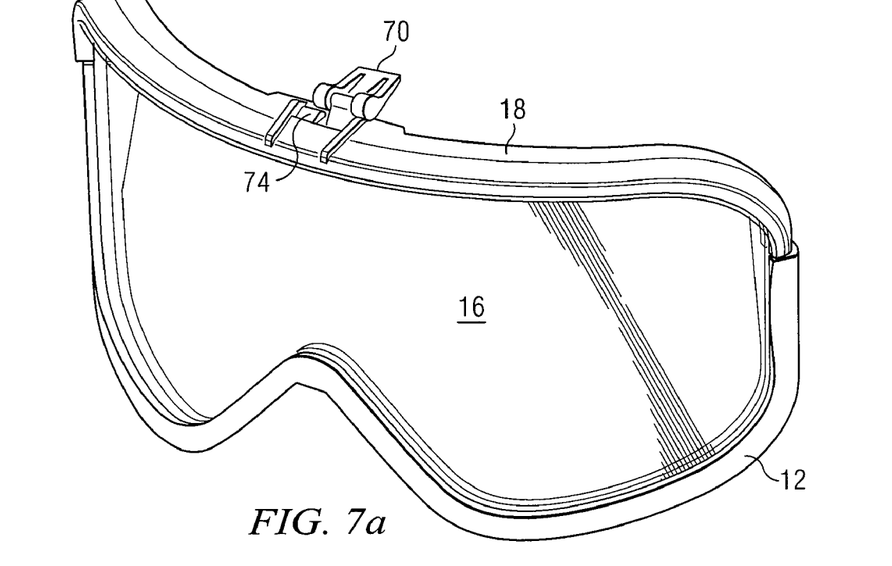
FIGS. 7(a) and 7(b) are drawings illustrating a variation of a top-mounted fastener embodiment of the lens replacement system.
Figure 7B:
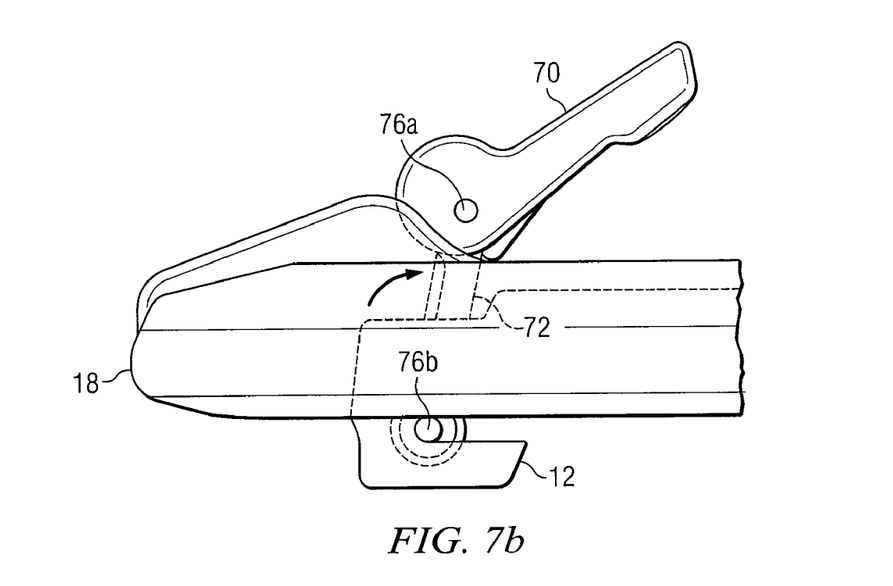
Figure 8:
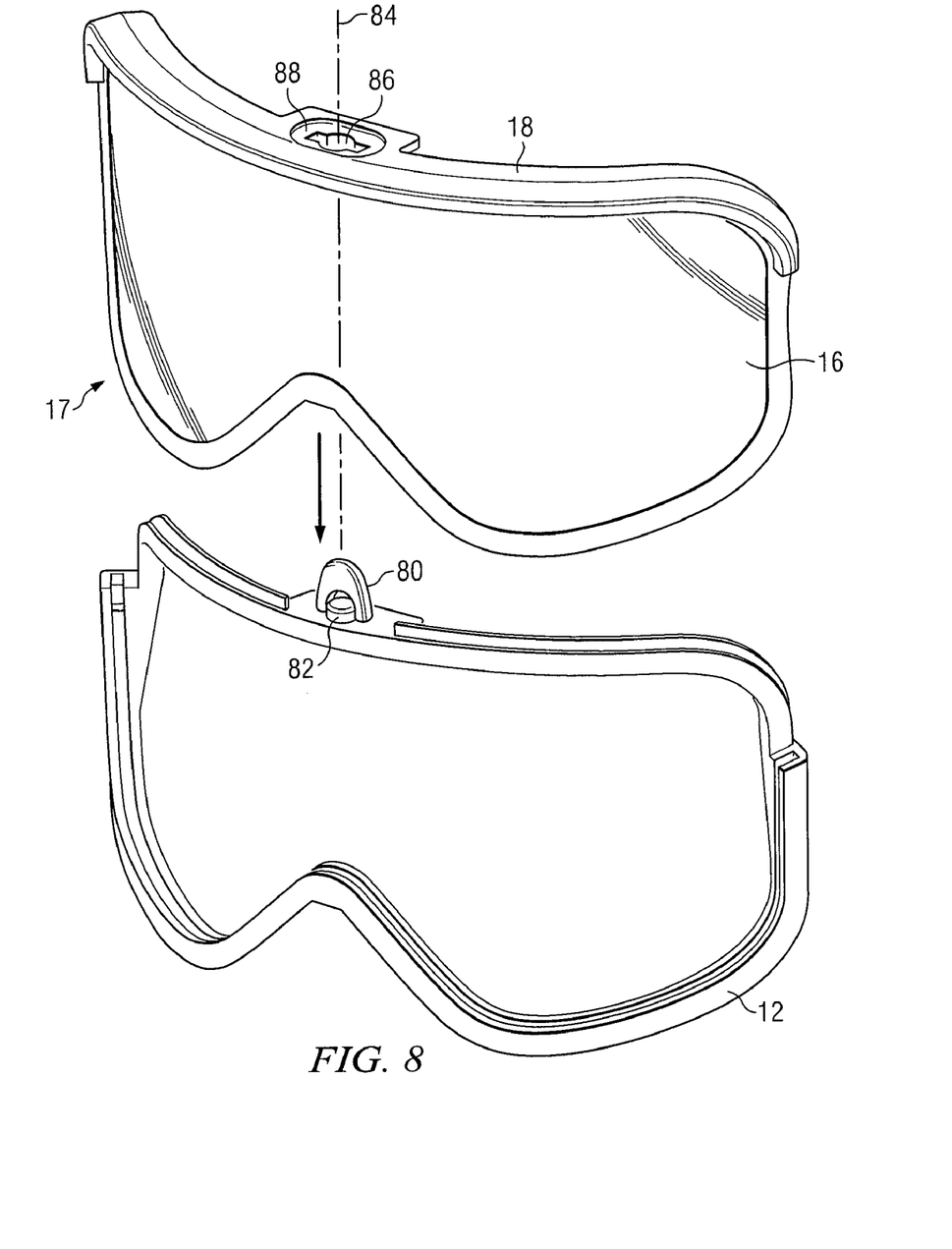
FIG. 8 is a drawing illustrating another variation of the top-mounted fastener embodiment of the lens replacement system.

FIGS. 6-8 illustrate a quick change lens replacement system implemented using various top-mounted fasteners to secure the lens. While the directional term "top" is used to describe the feature, it is not intended to limit the scope of the invention. One skilled in the art would readily recognize that such a feature could be bottom-mounted. Further, while several examples of fastening mechanisms are particularly described, a fastener could comprise any feature that is functional to secure the lens.

With reference to FIG. 6, an embodiment of a lens replacement system wherein a latch 36 is used to secure lens/top rail assembly 17 is illustrated. Latch 36 is mounted to frame 12 (specifically, to lens support 14 in the illustrated embodiment). As illustrated, latch 36 may be spring loaded such that in the "open" position, it is naturally raised out of the insertion/removal path of lens/top rail assembly 17. When lens 16 is properly positioned in frame 12, latch 36 may be rotated downward and clipped onto top rail 17. At this point, latch 36 is in the "closed" position. When latch 36 is in the closed position, lens/top rail assembly is securely affixed to frame 12. From the closed position, lens/top rail assembly 17 can be removed by unclipping latch 36 and pulling top rail 17 away from frame 12.

FIGS. 7(a) and 7(b) illustrate a variation of the top-mounted fastener implementation of a lens replacement system in accordance with the present invention. As with the embodiment in FIG. 6, lens/top rail assembly 17 is inserted from above, however, the fastening mechanism uses a cam profile to secure lens/top rail assembly 17 to frame 12.

A cam mechanism is implemented using latch 70 and link 72. As depicted in the present embodiment, top rail 18 has a contour 74 that mates with the profile of latch 70. Referring to FIG. 7(b), link 72 is pivotally connected to latch 70 and frame 12 at pivot points 76a and 76b In the illustrated embodiment, link 72 is spring loaded to rotate in a rearward direction about pivot point 76b. Spring loading latch 72 about pivot point 76b places a rearward force on latch 70 at pivot point 76a. The rearward force in combination with the contours of top rail 18 and latch 70 cause latch 70 to exhibit over-center behavior. Thus, latch 70 has two low energy states: 1) fully open; and 2) fully closed. A peak energy state exists when latch 70 is between fully open and fully closed. The primary benefit of the over-center behavior is that latch 70 has two preferred orientations: opened or closed. Accordingly, when opened, latch 70 will rotate to the position shown in FIG. 7(a). Further, when latch 70 is in a closed position, the low energy state ensures that lens/top rail assembly 17 is secured to frame 12. Because no intermediate latch position is useful in removing or installing lens/top rail assembly 17 the over-center behavior of latch 70 simplifies the lens replacement process.

FIG. 8 illustrates another variation of the top-mounted fastener embodiment of a quick change lens replacement system. As with the previous embodiments, lens/top rail assembly 17 is slidably associated with frame 12. The mechanism used to secure lens/top rail assembly 17 to frame 12 comprises folding latch 80 and screw 82. Folding latch 80 is pivotally connected to screw 82. Screw 82 is affixed to frame 12 and is rotatable about an axis 84 which is generally in the same plane as the lens/top rail assembly 17 installation/removal direction.

In the embodiment represented in FIG. 8, top rail 18 has an aperture 86 capable of receiving folding latch 80. More particularly, folding latch 80 may be inserted through aperture 86 when it is generally in the same plane as the lens/top rail assembly 17 installation/removal direction. Top rail 18 also has a contour 88 shaped in the profile of folding latch 86.

To secure lens/top rail assembly 17, folding latch 80 is initially inserted through aperture 86. Next, screw 82 is rotated to a point at which folding latch 86 overlaps lens/top rail assembly 17. The rotation causes screw 82 to lower into frame 12 thereby tightening folding latch 80 against top rail 18. At this point, lens/top rail assembly is secured to frame 12. Next, folding latch 80 may be lowered such that it is substantially coplanar with top rail 18. In the illustrated embodiment, top rail 18 has a contour 88 shaped in the profile of folding latch 80. Accordingly, when folding latch 80 is in a closed position it fits substantially within top rail 18.

Although the present invention has been described in detail with reference to particular embodiments, it should be understood that various other changes, substitutions, and alterations may be made herein without departing from the spirit and scope of the present invention. For example, although the present invention has been described with reference to various specific fastening mechanisms for securing lens 16 to frame 12, the invention should not be limited to such. In addition, it is foreseeable that one might combine several of the fastening mechanisms in a single embodiment of the present invention. Further, numerous other changes, substitutions, variations, alterations, and modifications may be ascertained to one skilled in the art and it is intended that the present invention encompass all such changes, substitutions, variations, alterations, and modifications as falling within the spirit and scope of the appended claims.

What is claimed is:

1. An eyewear system, comprising:
a frame, the frame comprising:
   a lens channel configured to slidably receive a lens;
   an opening to allow the lens to be inserted into the lens channel;
   a lens configured to be slidably received into the lens channel of the frame;
a top rail affixed to the lens; and
a latch pivotally coupled to the frame and configured to releasably secure the lens in the frame;
wherein the top rail comprises a latch catch configured to receive the latch.

2. The eyewear system of claim 1, further comprising:
an outrigger that includes the latch, the outrigger pivotally coupled to the frame; and
a head strap, wherein the head strap is affixed to the outrigger, the head strap operable to secure the eyewear to a face.

3. The eyewear system of claim 2, wherein the outrigger is configured to secure the lens in the frame.

4. The eyewear system of claim 2, wherein the latch is operable to restrain the outrigger in a locked forward position, wherein positioning the outrigger in the locked forward position secures the lens in the frame.

5. The eyewear system of claim 1, wherein the frame comprises an over-molded lens support, the lens support comprising the lens channel.

6. The eyewear system of claim 1, wherein the latch is coupled to a center portion of the frame.

* * * * *